United States Patent
Pingel et al.

(10) Patent No.: US 6,392,754 B1
(45) Date of Patent: May 21, 2002

(54) METHOD AND APPARATUS FOR MEASURING THE PROFILE OF REFLECTIVE SURFACES

(75) Inventors: Ulrich Pingel, Marl; Matthias Dümmler, Recklinghausen; Johannes Klaphecke, Gelsenkirchen, all of (DE)

(73) Assignee: Innomess Gesellschaft fur Messtechnik mbH, Marl (DE)

( * ) Notice: Subject to any disclaimer, the term of this patent is extended or adjusted under 35 U.S.C. 154(b) by 0 days.

(21) Appl. No.: 09/284,527

(22) PCT Filed: Oct. 17, 1997

(86) PCT No.: PCT/EP97/05732

§ 371 Date: Jul. 6, 1999

§ 102(e) Date: Jul. 6, 1999

(87) PCT Pub. No.: WO98/17971

PCT Pub. Date: Apr. 30, 1998

(30) Foreign Application Priority Data

Oct. 18, 1996 (DE) .......................... 196 43 018

(51) Int. Cl.$^7$ .............................. G01B 11/24
(52) U.S. Cl. ..................... 356/603; 356/239.1
(58) Field of Search .................. 356/376, 375, 356/371, 239.1, 374, 601, 602, 603, 604, 606, 610, 612, 623, 239.3; 382/108; 250/559.22, 559.23

(56) References Cited

U.S. PATENT DOCUMENTS

| | | | |
|---|---|---|---|
| 3,799,679 A | * 3/1974 | Simko | 356/239.1 |
| 4,508,452 A | * 4/1985 | DiMatteo et al. | 356/376 |
| 4,634,278 A | * 1/1987 | Ross et al. | 356/376 |
| 4,794,550 A | * 12/1988 | Greivenkamp, Jr. | 356/376 |
| 4,929,846 A | * 5/1990 | Mansour | 356/371 |
| 5,110,200 A | 5/1992 | Snook | |
| 5,237,404 A | * 8/1993 | Tanaka et al. | 356/376 |

FOREIGN PATENT DOCUMENTS

| | | |
|---|---|---|
| DE | 24 39 988 | 3/1976 |
| DE | 44 01 541 A1 | 7/1994 |
| EP | 0 262 089 A2 | 3/1988 |

OTHER PUBLICATIONS

"Schnelle Planitätsmessung von grossflächigen Objekten" (Rapid planarity measurement of large–area objects), MSR–Magazine, Nov. 12, 1995, pp. 16–18.

"Weld Bead Placement System for Multipass Welding", J. Wu, J.S. SMith, J. Lucas, Proc.–Sci Meas. Technol. vol. 143, No. 2, Mar. 1996.

"Streifenprojection Prüft in Echtzeit mit 5 μm Auflösung", Werkstatt und Betrieb, 128 (1995) 3, pp. 157–160.

"Measurement of the 3–D Shape of Specular Polyhedrons Using an M–Array Coded Light Source", 8096 IEEE Transactions on Instrumentation and Measurement, 44(1955) Jun., No. 3, New York, US, pp. 775–778.

* cited by examiner

Primary Examiner—Hoa Q. Pham
(74) Attorney, Agent, or Firm—Nikolai & Mersereau, P.A.

(57) ABSTRACT

The invention concerns a method of measuring the course of a reflective surface of an object including the steps of projecting a defined pattern of at least two different light intensities onto the surface to be measured; observing at least one section of the surface by at least one camera; and evaluating the observed section on the basis of the camera data. The invention provides a simply designed and accurately controllable method in that the pattern produces a mirror image in the reflective surface, and in that the observed section includes a section of the mirror image of the pattern. The invention further concerns an instrument for determining the course of the reflective surface of an object, the instrument including a device for generating a light pattern and having at least one camera for observing at least one section of the surface. The invention provides a simply designed and accurately controllable instrument in that the camera is adjusted precisely to a mirror image of the light pattern.

20 Claims, 4 Drawing Sheets

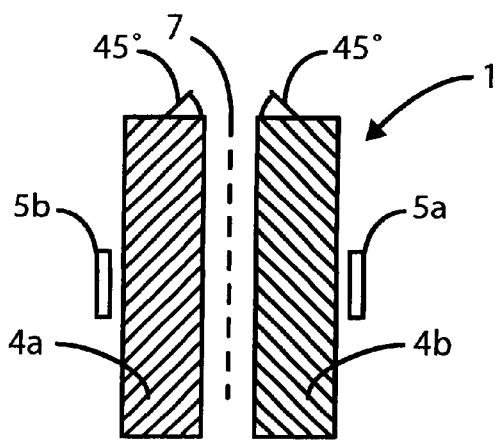
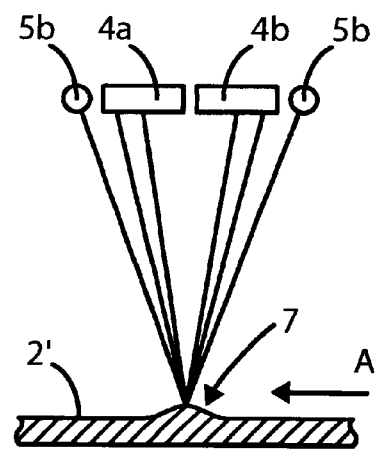
FIG. 5  FIG. 6
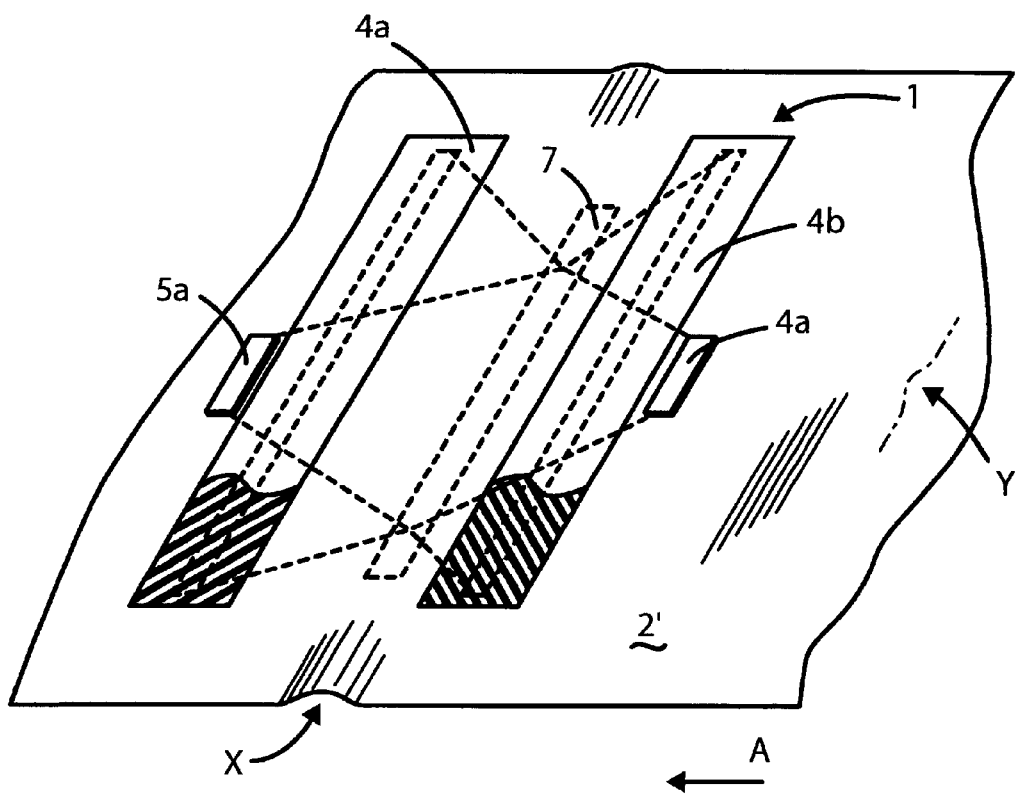
FIG. 7

METHOD AND APPARATUS FOR MEASURING THE PROFILE OF REFLECTIVE SURFACES

DESCRIPTION

1. Technical Field

The invention relates to a method for measuring the profile a reflective surface of an object, comprising the steps of projection of a defined pattern composed of at least two different light intensities onto the surface to be measured; observation of at least one section of the surface by means of at least one camera, and evaluation of the observed section based on the camera data. The invention furthermore relate to an apparatus for determining the profile and other characteristics of the reflective surface of and object having means for producing a light patter, and having at least one camera for observing at least one section of the surface.

2. Prior Art

A number of scanning methods for measuring the profile of surfaces of flat or curved objects are known from practice, in the case of which methods, for example, scanning elements which can be extended pneumatically are moved into contact with the object to be measured and supply to an arithmetic and logic unit a signal which corresponds to the movement carried out, which arithmetic and logic unit uses this signal to determine the local separation and, based on a large number of such measurements, to make a statement on the profile of the surface of the object. The use of such measurement methods and the associated apparatuses is complex since, bearing in mind the sensitivity of the object to be measured, the measurement probe can be extended only slowly, may possibly damage the object or its surface (for example scratching it or making an indentation) and, furthermore, the temperature range in which such techniques can be used is extremely limited. Such tactile measurement methods are thus generally inferior to non-contact measurement methods.

The article by Körner, K. et al., "Schnelle Planitätsmessung von groβflächige Objekten" [Rapid planarity measurement of large-area objects], MSR-Magazine, Nov. 12, 1995, pages 16–18 describes an optical measurement method for measuring the planarity of thin glass. In this case, based on a light source a line grid is imaged sharply on a thin-glass plate, with the optical axis at a large angle (84°) to the normal to the thin-glass plate. This image is observed from an angle which is also large using a CCD line-scan camera, from whose observation information about the height and/or about the planarity of the thin glass is calculated by means of phase-evaluating algorithms. A first imaging stage is provided between the line grid and the thin-glass plate in the optical direction of incidence, and a second imaging stage is provided between the thin-glass plate and the line-scan camera in the optical direction of reflection. The first imaging stage images the line pattern of the line grid on the front face of the glass, while the second imaging stage in turn produces a sharp representation of the image on the line-scan camera. The known technique has a number of inadequacies: on the one hand, the geometric arrangement of the components is complex since the optical axes from the imaging stages strike the thin-plate glass at a very flat angle. The light emerging from the line grid is imaged via the first imaging stage on the glass plate; the line grid itself is inclined with respect to the optical axis, so that the distances between the lines turn out to be different. If minor changes are made to the position of the thin-glass plate which is currently being measured and thus cannot be assumed to be constant, the entire device must be readjusted. However, the calculated values are subject, at the least, to a severe error tolerance. Since even very small discrepancies in the planarity to be measured of an ideal-planar surface lead to severe distortion of the image of the line grid, the resolution of the apparatus is limited. Furthermore, such an apparatus also occupies a large amount of space, so that high space costs are incurred when such an apparatus is used for on-line measurement. Space problems may occur in particular after such apparatuses have been re-equipped. Finally, it should also be mentioned that the line-scan camera is very sensitive to stray light, as a result of which costly screening must be provided; this is due to the fact that the image is produced sharply on the camera, with the camera being arranged at an angle to the glass surface, since the measurement point would otherwise be outside the field of view, so that the camera can also be influenced by other light (and variations in it). In order to evaluate the measurements, the imaging conditions must be known and must be taken into account. If one wishes to carry out a three-dimensional measurement using the known technique, this can be done only by moving the glass plate relative to the image section which the camera is observing, and carrying out a number of measurements successively. The technique is not designed to carry out measurements at a number of points on the surface at the same time, since a sharp image of the line grid is produced in only one area. In consequence, exact measurements take a time in the order of magnitude of one to several minutes. The imaged pattern can no longer be evaluated for measurement of surfaces with relatively large radii.

U.S. Pat. No. 5,110,200 describes a method and an apparatus for observing and for measuring the human cornea. A video image of a reflection of an illuminated ring is in this case examined for discontinuities in the brightness of the image, in order to determine the contour of the cornea. However, this method is not suitable for moving objects, such as moving conveyor belts, since evaluation is impossible when a large number of changes take place at the same time. Furthermore, the method is likewise not suitable for evaluating objects which reflect light a number of times, as is the case for the two surfaces of a glass pane. The known method can also not determine discrepancies in the planarity of a surface. Finally, the known method is very time-consuming, so that it is not suitable for industrial use.

DE-A-44 01 541 likewise describes a method for determining the surface structure of the cornea. In this case, a camera which is arranged behind a perforated shutter detects the light which is emitted from a light-emitting diode (which moves on circular paths with variable radii) and is reflected from the surface of the retina. Local defects in the retina are detected from discrepancies in the circular shape of the reflected light. Where reflections merge into one another or are interrupted, the observation can be carried out intermittently over a period of time to allow these reflections to be associated with the respective output radius of the light-emitting diode. The known method is time-consuming and can thus not be used on an industrial scale. It is also not suitable for double-reflecting materials. Furthermore, it is impossible to superimpose a movement of an object to be measured on the movement of the light source.

SUMMARY OF THE INVENTION

The invention is based on the object of providing a technique (method and apparatus, respectively), for measuring the profile of a reflective surface of an object which is of simple design and can be used with precision.

This object is achieved according to the specification, drawings and claims herein in that the pattern produces a mirror image in the reflective surface, and in that the observed section comprises a section of the mirror image of the pattern, and according to the description of the apparatus in that the camera being set such that it is focused on a mirror image of the light pattern:

The technique according to the invention makes it possible, in particular, to measure the profile of a reflective surface of an object which is composed of a material which is at least partially transparent for light at specific wavelengths and which reflects this light on at least one further surface arranged behind the surface. Examples of such objects are glass plates, plastic sheets, reflective surfaces covered with a transparent coating, laminated car window panes, etc. The mutually superimposed reflections from the at least two surfaces are advantageously separated, so that measurements are obtained with a precision not achieved before.

It is not only possible for the camera to observe the mirror image directly, but also for the camera to observe the mirror image indirectly via a mirror arrangement.

Expediently, in the former case, the optical axes (planes) then include an angle which is less than 90°, preferably (very) much less, between the pattern and the mirror image on the one hand, and between the mirror image and the camera on the other hand. The two optical axes are preferably arranged such that they include the same angle on both sides of the normal to a planar surface as the angle of incidence and the angle of reflection of light with respect to said normal, with the total of these angles giving the included angle. It is possible and preferable for this included angle to be very small. The aperture angle between the pattern and camera is the angle (on the planar surface) between those planes on which the line-scan camera and the observed mirror image section on the one hand, and the light pattern and the observed section on the other hand, are arranged. In the case of a matrix camera, the corresponding angles are preferably close to one another for each line.

In the second case, in which a mirror arrangement is provided, the latter preferably comprises a parabolic mirror which always images the observed mirror image sharply, irrespective of the distance between the reflective surface and the parabolic mirror, at a point at which the camera is then arranged.

A pattern which is easy to produce has equidistant, alternately bright and dark light strips; however, other geometrically defined alternating light/dark sequences are also suitable for use as a pattern, for example those having strips which have more than two different light intensities, checkerboard patterns, and cross-hatched patterns. One particularly advantageous pattern comprises dark (light) strips which cross one another at right angles and enclose light (dark) squares whose edge length corresponds to the width of the strips.

According to the invention, the pattern is reflected directly in the reflective surface. Planarity faults (that is to say small height changes) in the measured two-dimensional or three-dimensional reflective surface cause distortion in the mirror image, with a minor projection or indentation in the surface inducing a broader or, respectively, a narrower mirror image in that the incident light is somewhat more strongly compressed or scattered. Using the, camera, it is possible to detect the intensity change (and/or the profile) in the light/dark mirror image precisely for each point in the mirror image, and thus to evaluate even very small changes in the degree of brightness, and, for example by forming the differences to an ideal mirror image, to draw conclusions about variations in the surface to be measured. The local inclination differences are calculated on the basis of boundary changes in the dimensions of the light/dark intervals observed by the camera. The simple design of the apparatus according to the invention and the compact and direct method according to the invention allow the surface profile to be recorded extremely quickly and reliably. The light originating from the pattern is parallel when it arrives at the surface to be measured. The light/dark sequence of the pattern is reflected in the surface. If the surface were completely planar, this would accordingly result in a mirror image that is exactly proportional to the light/dark pattern—provided the lateral offset from the normal is not too large. Since the design of the mirror image (distances etc.) is known, the arrangement according to the invention advantageously makes it possible for the discrepancies from an ideal image to be calculated with respect to the known dimensions of the line grid rather than in comparison with a recorded image of a normal surface, as a result of which the accuracy of the evaluation is improved. The amount of distortion of a strip in the observed mirror image is measured, and this is used to determine its inclination with respect to a planar surface, with the capability to express the inclination as an angle. The inclination of the corresponding area element in the mirror image can thus be determined for each strip in the pattern; if these elements are arranged in a row (integration), starting from a defined point (for example as a result of contact) on the surface, information is also obtained about the successive height rise occurring as a result of the inclinations, and the profile can thus be "followed".

BRIEF DESCRIPTION OF THE DRAWINGS

FIG. 5 shows a schematic plan view of a further exemplary embodiment of an apparatus according to the invention.

FIG. 6 shows a schematic side view of the apparatus shown in FIG. 5.

FIG. 7 shows a schematic perspective view of the apparatus shown in FIGS. 5 and 6.

DETAILED DESCRIPTION

Figure 1:
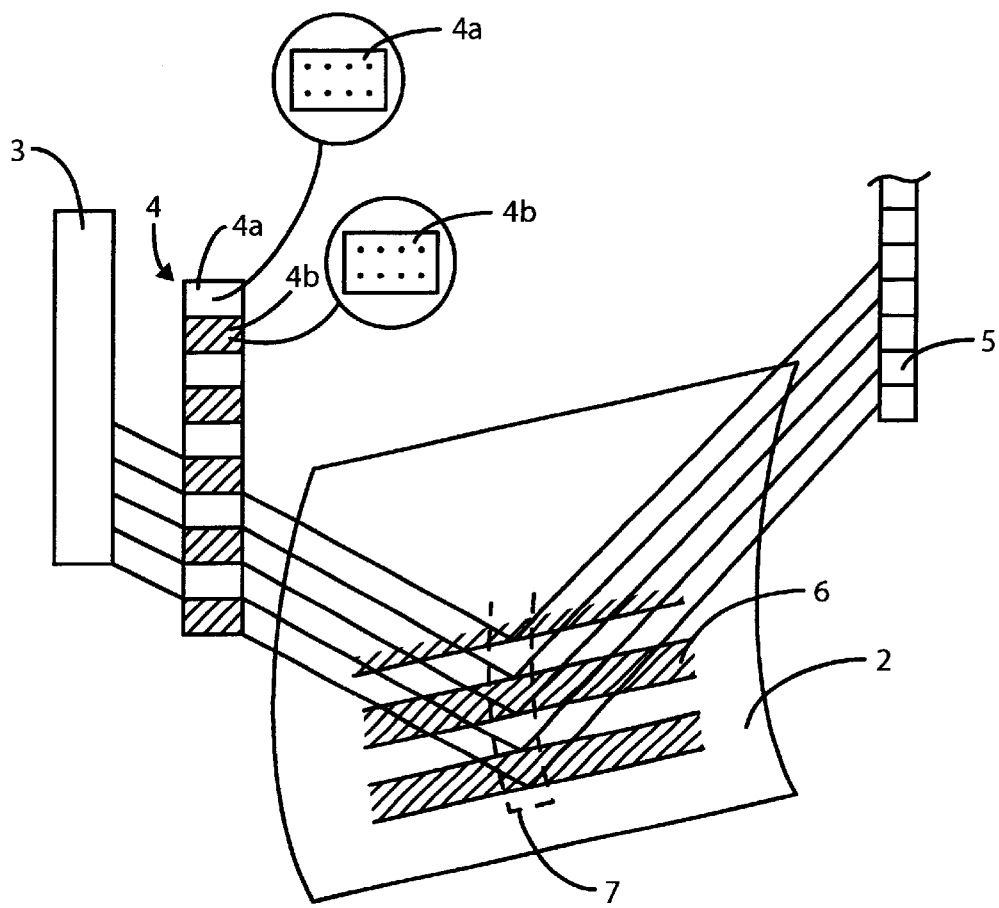
FIG. 1 shows a schematic illustration of an exemplary embodiment of the invention.

Further advantageous developments of the invention result from and will occur to those skilled in the art based on the following description and from the appended claims. The invention is explained in more detail in the following text with reference to exemplary embodiments illustrated in the attached figures.

It should be noted that the invention and its developments are suitable both for measuring planar reflective surfaces such as flat glass and for measuring reflective surfaces, for example polished surfaces, which have a multidimensional sphere, for example vehicle window panes, stamped parts, cathode ray tubes, objects coated with a reflective coating and the like, in which case the objects may be composed not only of rolled, drawn and float glass, but also of acrylic glass or PVC.

One very interesting special case of measurement of the profile of a surface is measurement of a planar surface in order to determine its planarity. This information is required in a large number of businesses carrying out processing operations. The method according to the invention and the apparatus according to the invention are also suitable for this purpose. In principle, the same evaluation can be used; however, a limit-value analysis is preferably carried out, in the case of which the change in inclination angle is determined over a distance. It is then also possible to investigate the accuracy of the surface processing of an oblique surface, without the oblique surface itself being evaluated as an undesirable inclination. The average inclination angle can also be derived from this. The evaluation process described above can be used to examine the smoothness of all "continuous" surfaces, for example even for examining how spherical a sphere is. Minima, maxima and points of inflection in the differentiations provide high sensitivity for indicating points with "non-smooth" or non-planar profiles.

The pattern can be produced cost-effectively both by arranging a light source and a physical grid one behind the other and by means of a matrix composed of a large number of LEDs.

According to a first preferred variant, the light pattern which is used is a structure of at least two different light intensities which are arranged regularly and alternately. In order to obtain optimum contrast, according to a first preferred development, a line grid composed of equidistant lines which are alternately opaque (light permeability approx. 0%) and transparent (light permeability approx. 100%) is used such that the light which, originating from a light source, passes through the transparent line in parallel form to the reflective surface produces, with the light which is impeded by the opaque line as it passes through the light grid, a sequence of mutually alternating light and dark lines or strips, which are reflected in the surface. It is self-evident that the light permeability can be limited to light at a specific wavelength or in a wavelength band. Alternatively, according to an alternative advantageous variant, it is also possible to design the light grid in such a manner that it has more than two different light permeabilities in sequences, for example 0%–50%–100% or 1%–10%–100%.

Depending on the distance between the camera, which is preferably a line-scan camera or matrix camera, and the image, a measured value is obtained for each pixel in the camera and is expressed either by an observed dark line or an observed bright line in the mirror image, or by a gray level in the transition region between two lines. If these measured values are compared with the values of an ideal image (and assuming that the light profile is parallel, which assumption is acceptable, to a first approximation, without any loss of accuracy, as a result of which the comparison with the light pattern itself can be carried out directly), then locally definable discrepancies from a true-to-scale light pattern are obtained directly. These discrepancies can be used to calculate exactly even very small inclinations deviating from a planar surface, and these can be determined in an evaluation unit, for example using a software routine. In this case, the relative position of the observed light/dark sequence is advantageously evaluated so that any oblique surface in the arrangement of the surface which is otherwise itself planar does not adversely affect the measurement.

According to a second preferred variant, the light grid is a cruciform grid which essentially looks like a line grid in which, for example, the opaque lines also run at right angles to the first line direction. This results in a cruciform grid, one quarter of which is permeable to light, and three quarters of which is impermeable to light. However, alternatively, it is possible to enlarge the light-permeable area which is surrounded by light-impermeable rectangles in the light grid, in such a manner that the ratio of light to dark is roughly equal. Here, furthermore, it is also possible to provide more than two light permeabilities. A flat camera can in this case be used to observe the mirror image, that is to say a matrix camera which observes a rectangular, two-dimensional section of the surface, and thus allows a 3-dimensional measurement (the planarity discrepancy (inclination, ripple, height) in the surface, calculated from the measured values, corresponds to a first dimension; this value is measured over the coordinates in the longitudinal and lateral directions, so that the surface can be represented as a three-dimensional image; a measurement with a line-scan camera would produce a 2-dimensional measurement: profile against length, which is worthwhile, for example, for certain vehicle body-work metal sheets).

According to a third variant, it is possible to design the light grid as a checkerboard structure, in which opaque and light-permeable squares are formed alternately.

According to a fourth variant, the sequences of light intensities achieved in the previous variants are produced by a matrix composed of LEDs, which may be designed in a similar manner to a stadium display in a sports arena.

One common feature of the methods described above is that they compare the observed mirror image against the known dimension of the grid, and use observed discrepancies to deduce the angle through which the surface is inclined, for example, with respect to a planar surface.

A high-precision measurement of the planarity and/or the smoothness and the ripple of the surface of a reflective surface, whose accuracy and resolution are improved once again by a factor of 10 to 50, can be achieved by an advantageous version: the mirror image of the grid is likewise observed using a line-scan camera or matrix camera, but in such a way that a light/dark sequence of the pattern, preferably an equidistant light/dark pair which is produced, for example, by means of an opaque and transparent light grid like the cruciform grid mentioned above, is imaged onto a number of pixels of the camera in each case for each dimension, this number being an integer multiple of the sequence. This results in moire fringes on the "grid" of the camera which, using a phase-evaluating method, allow extremely accurate statements to be made about discrepancies in planarity. During evaluation, the detected moire image is converted into a sine wave (or some other cyclic curve) that is typical of the moire image, and the phase shifts are used to deduce, on the one hand, the compressions and expansions of the calculated sine wave and, on the other hand, planarity errors, ripple and the like.

The relationship of a light/dark pair to three, or alternatively four or five, pixels is particularly preferred. Owing to the high costs of matrix cameras, it is expedient to minimize the number of pixels per light/dark sequence.

In the case, for example, of a grid having a checkerboard pattern composed of light and dark squares and using a matrix camera, this means that there are nine pixels on four squares. The pixels are directed at the image in such a manner that, in the ideal case, one pixel observes a complete bright point and another pixel observes a complete dark point, while the pixel in between sees a gray tone. If changes now occur in the surface planarity, the image is shifted as a function of the variation, and the light/dark values which are seen by the pixels are shifted by a specific amount in one direction or the other. This amount can be determined particularly easily from the intensities which the pixels measure and, using simple evaluation methods, lead back to an angular shift, which is an expression of the planarity. Information about the planarity can be determined with considerably improved resolution by virtue of moire image phenomena, which occur as a result of the superimposition of the light grid and the "grid" of the line-scan camera.

It is also possible to image the mirror image of a light/dark sequence on just two pixels, as a result of which the camera, in particular a matrix camera, becomes very much cheaper. Then, however, the light grid must be designed in such a manner that sequences of lines are produced which are repeated using at least three different light intensities. This relationship also allows a sine wave to be determined, whose phase shift in the moire fringe that is formed can be used to determine planarity errors.

Finally, it is also possible to image the mirror image of a light/dark sequence, in particular of a pair as well, on one pixel or on a multiple thereof; however, three records are then required, in each of which the pattern is shifted by one-third of a light/dark sequence. This shift can easily be achieved using the already described matrix of LEDs.

In the case of materials which are at least partially transparent, and based on a separate measurement of the light beam reflected on the lower face and on the upper face of the glass, it is furthermore possible (in addition to analyses of the height and ripple) to draw conclusions as well on the optical refractive index of the material, such measurements otherwise being possible only using transmission methods. Thus, according to a particular advantage of the invention, it is possible to isolate from a plurality of mutually superimposed reflections that reflection which originates from the rear face of the material, and for which the illuminated pattern (and/or the illuminated parts of the pattern) has passed through the material. This reflection on the "rear face" turns out (for example owing to loss of light which is not reflected) to be weaker, so that it can easily be isolated. However, the reflection on the rear face furthermore, after differentiation, provides a statement about the reflection optics of the material.

The measurement with the methods and/or apparatuses according to the invention is very fast, its order of magnitude being only a few milliseconds. It is thus advantageously possible even to observe and to measure a material "while moving", for example at the outlet from a rolled glass plant or endless rolling of reflective steel. When using a cruciform grid with a matrix camera, it must be remembered that, in contrast to a line-scan camera which reads the bits in parallel form, matrix cameras are, as a rule, read in serial form. Since the time interval between two reading processes may possibly be too long if the feed rates of the surface to be measured are high, it is possible to shorten the illumination by means of the light grid using a stroboscope or flash. If, in contrast, the surface is stationary, a line-scan camera can preferably be used to scan the entire surface, using this to determine a virtually three-dimensional representation.

The evaluation step preferably takes account of the fact that the distance between the line-scan camera and the surface to be measured is not entirely uniform over the line in the camera, since the line-scan camera has a shorter extent than the extent of the mirror image being observed. Accordingly, in the direction of the mirror image, the camera has an aperture angle which in general is very small, but leads to a certain measurement inaccuracy (resulting from lack of clarity and resulting from the greater distance), which is taken into account in the evaluation of the image and is essentially compensated for even at this stage by the scale ratio onto the camera. What has been said above likewise applies to both dimensions when a matrix camera is used.

According to a particularly preferred development of the invention, it is possible to measure transparent mirror materials as well, for example cathode ray tubes, displays, plate glass, mirrors, curved glass or toughened or laminated safety glass. Such materials have the property that they reflect incident light both on their upper face and on their lower face, and thus emit a double image. The image from the upper face, whose intensity is generally somewhat stronger than the image from the lower face, has the image from the lower face superimposed on it. While the prior art attempts to eliminate the image from the lower face by using an incidence angle that is as flat as possible, means are preferably provided which allow the image from the lower face to be taken into account in the evaluation.

According to a first variant of these means, this is achieved in such a manner that the representation of the image on the camera is unfocused, so that both reflected images are taken into account with their resultant intensity, and the camera detects a signal which respectively originates from both mirror images. In this case, it is necessary to take account of the fact that, owing to the thickness of the glass, the light paths are of different lengths and, in consequence, a corresponding offset occurs which results in "blurred" regions being formed between a light region (superimposed reflection of the transparent strip) and a dark region (superimposed reflections of the opaque region of the grid), in which blurred regions the "reflection" of a dark region (to be more precise, darkness is not actually reflected, but the corresponding dark strip is bounded by two reflected light strips) from one side of the glass has the reflection of the light region from the other side of the glass superimposed on it (and vice versa). The distance between these regions depends on the angle at which they are observed; this angle is known and must be taken into account in the evaluation. In this case, when a light grid region is reflected on the upper face, the intensity of the detected image will be somewhat greater than in the converse case.

As an alternative to this, and preferably, it is possible to provide two line-scan cameras or matrix cameras arranged one behind the other, which preferably observe the same image section, with one camera in each case being set such that it is focused on the mirror image in each case reflected from one side of the transparent material (focus on grid). The individual evaluation can then be carried out, knowing the thickness of the object.

By providing two cameras, preferably at different heights and/or at different angles with respect to the surface, it is furthermore possible—both for transparent and opaque surfaces—to discriminate whether a change in the number of light/dark sequences observed in an image section is caused by the curvature of the surface (lens effect) or by a change in the height at which the reflective surface is arranged (which results in the proportionality factor between a defined pattern and the mirror image being influenced).

In principle, it is preferable to separate the reflection signals on materials such as glass which produce two reflections. This is because, apart from the more accurate individual information which allows a statement to be made about the "front" surface, it is also possible, for example by means of an integration step, to make a statement about the shape, and by differentiation of the measured values which have been reflected from the "rear" surface, a differentiation step allows a statement to be made about the reflection optics at the point of the respective measured material.

A particularly expedient type of observation of the same section is possible if a semireflective mirror is provided, which makes it possible to observe the same section with different cameras from different distances. If, for example, an increase in the number of light and dark strips is observed in one image section, then, assuming that the height of the surface is fixed, this would indicate curvature in the surface, like a concave lens. On the assumption of a completely planar surface whose distance to the pattern and to the camera is, however, subject to a fluctuation, the increase in the number of strips observed in one section would indicate an increase in the distance to the pattern or camera as a result of the lengthened beam paths resulting from this. A corresponding situation applies to a fixed reduction in the observed number. In practice, particularly if the object having the surface to be measured is measured while it is moving, both influencing factors are superimposed, but it is particularly advantageous for the calculation of the profile if errors resulting from fluctuations in the height can be eliminated. In this case, it should be noted that the cameras for monitoring the same image section from different distances have a correspondingly different aperture. However, this means that, in the event of a discrepancy in the height of the surface, the number of strips observed by each of the two cameras varies in proportion to the ratio of the discrepancy/distance.

The evaluation of the image section observed by the two cameras can then preferably be carried out such that the discrepancy between the two in the number of strips absolutely observed is used in a first step to determine the actual height, and the number of strips observed by at least one of the cameras in a further step with respect to the expected number for the determined height is used to determine the curvature, taking into account the appropriate proportionality factor.

The evaluation, according to the invention, of the surface of an object which is at least partially reflective, by means of a matrix camera, is admittedly advantageous in terms of evaluation but, beyond certain orders of magnitude, matrix cameras are really expensive to buy. If essentially planar materials are being measured, that is to say the measurement relates primarily to investigation of planarity, virtually the same assessment validity can be achieved as with a matrix camera by means of a particularly preferred development of the invention for which only two line-scan cameras are required. In this case, the reflection of two light grids is in each case observed at the same point on the surface by in each case one camera. The light/dark sequences of the light grids are, however, arranged inclined, preferably at 45° to the material transport direction, and at an angle that is complementary to this to form 90°, that is to say preferably once again 45°, with respect to their longitudinal axis. Furthermore, the oblique angles of the two light grids are exactly opposed, that is to say they preferably cross at about 90°, and are thus inclined with respect to the mirror axis with the camera. If an (ideally typical) change in the reflection occurs in the surface, in such a manner that the reflection is deflected in a direction of the surface transversely with respect to the longitudinal extent of the grids, then the image detected by one of the cameras moves (in accordance with the trigonometric ratio) in a direction at right angles to the deflection direction by a proportional factor, while the other camera detects a movement in the direction opposite to this, at right angles to the deflection direction. In the other (ideally typical) case, in which compression or expansion in the reflection is detected in the longitudinal direction of the grid, the lens effect on which this change is based can be determined by evaluating the phase, as before. Since both cameras are observing the same section of the material, the two (ideal) discrepancy types can be discriminated directly and can be linked back to the corresponding point of reflection, so that "topography record" of the surface is possible. It is self-evident that, when continuous scanning is carried out using a device refined in such a manner, the surface may also remain stationary. This variant according to the invention is particularly suitable for measurements of objects which are moved in particular endlessly underneath the measurement apparatus.

Furthermore, evaluations are feasible in which the intensities at different wavelengths are taken into account, in particular by means of a color camera for the red, blue and green intensities, and in the case of tinted glass, which absorbs light of different color or at a different wavelength with a different intensity.

It should be noted that the invention and its developments are suitable both for measuring planar reflective surfaces such as flat glass and for measuring reflective surfaces, for example polished surfaces, which have a multidimensional sphere, for example vehicle window panes, stamped parts, cathode ray tubes, objects coated with a reflective coating and the like, in which case the objects may be composed not only of rolled, drawn and float glass, but also of acrylic glass or PVC.

Further advantageous developments of the invention result from the following description and from the dependent claims.

The invention is explained in more detail in the following text with reference to an exemplary embodiment which is illustrated in the attached figures.

With reference to FIGS. 1 to 4, 1 denotes an arrangement for measuring the profile of reflective surfaces. The reflective surface 2 to be measured is a 2.5 mm thick, curved rolled glass pane, which has a rectangular outline and a bend in the longitudinal direction. Light is projected onto the rolled glass pane 2 by a light source 3 which extends in a plane through a light grid 4. The light grid 4 is composed of equidistant, 5 mm wide strips or lines, which are designed to be alternately opaque and transparent. The parallel light which passes through the light grid 4 is thus arranged in (light) strips 4a, which are separated by respectively non-illuminated (dark, light intensity=0) strips 4b. As seen in the two detailed fragments of FIG. 1, these may be made up of a matrix of illumination sources such as LED's, for example, which are alternately illuminated and dark as is well known to those skilled in the art. It should be noted that, since the light is parallel when it leaves the grid 4, the width of the grid 4 essentially extends over a wide corresponding to the width of the pane 2, in order that the pane 2 is virtually completely covered with illuminated and unilluminated strips. The length of the grid 4, that is to say its extent transversely with respect to the strips and parallel to the short edges of the strips, is about 2 m, so that a total of 400 strips (200 light/dark pairs) are arranged side by side.

The same surface of the pane 2 faces a line-scan camera 5, which may be in a housing 8 together with matrix pattern light grid 4 (FIG. 3) and which covers a section of the mirror image 6 which is produced by the grid 4 in the surface of the piece of glass 2. The section is about 80 cm. The observed mirror image section which is indicated by the region 7 with dashed lines in FIG. 1 is located essentially centrally on the surface of the pane 2, and runs essentially centrally on the surface of the pane 2, and runs essentially at right angles to the extent of the light/dark strips in the mirror image 6. It can be confirmed that equidistant strips simplify the evaluation, but are not absolutely essential. Each of the pixels in the line-scan camera 5 detects the position and intensity of the observed mirror image 6 with high accuracy. The focus of the camera 5 is set to the grid 4 for this purpose.

Figure 8:
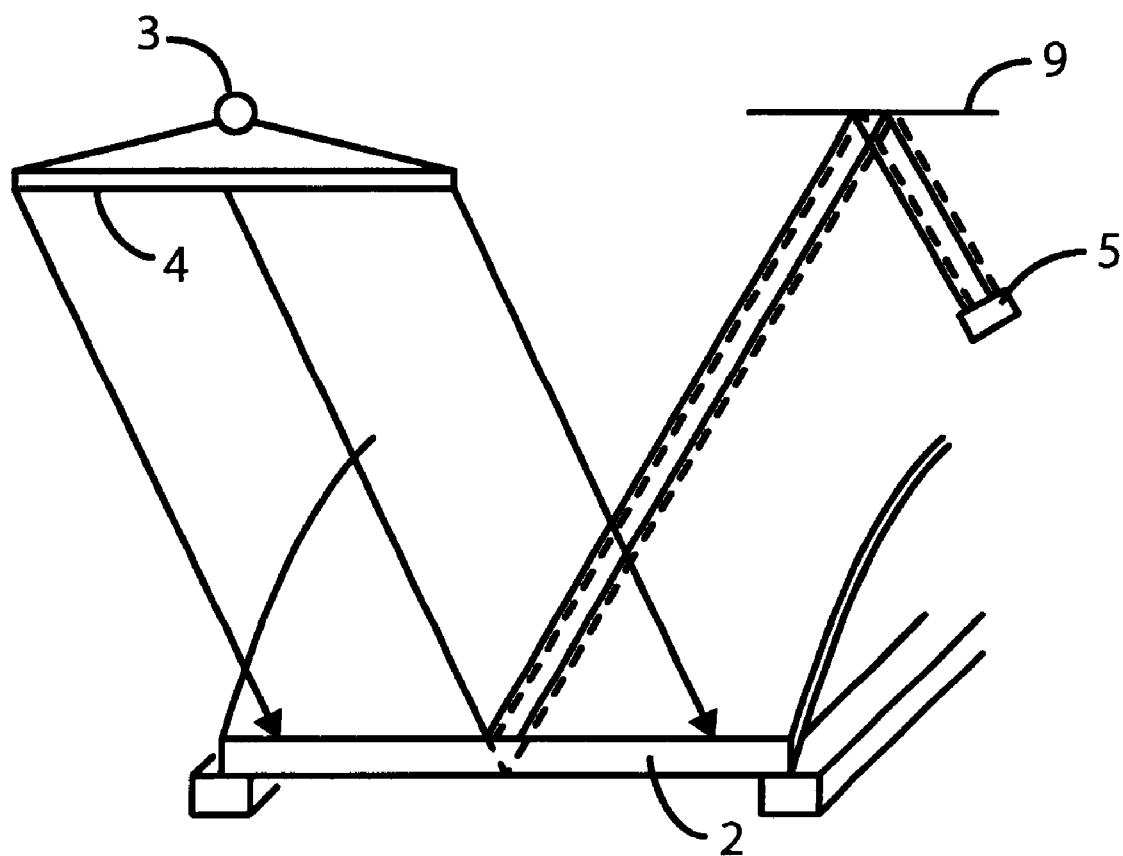
FIG. 8 is similar to FIG. 2 and shows a front view of the apparatus according to the invention including a mirror.

However, it is possible to observe the mirror image 6 in the surface 2 of the glass indirectly, for example via a mirror as at 9 in FIG. 8, rather than directly as described above. A mirror arrangement for indirect observation for this purpose preferable comprises a parabolic mirror. The parabolic mirror is arranged in such a manner that a section of the mirror image 6 is reflected back onto the camera. On the one hand, the image reflected by the parabolic mirror is always set such that it is focused onto the camera; on the other hand, this setting is independent of the distance between the parabolic mirror and the glass 2, so that the complexity of focusing the camera is advantageously reduced.

Assuming a completely planar surface, a mirror image 6 which is proportional to or identical to the corresponding grid 4 would be detected by the camera 5. However, if there are planarity differences on the surface of the glass 2, the mirror image 6 is distorted, that is to say the strips which are detected by the camera 5 are no longer at equidistant intervals. Discrepancies from a completely planar surface occur as angle differences in the surface 2, there being, so to speak, a profile of mountains and valleys, whose gradient is not zero (completely planar surface). The mirror image 6 of a measured surface 2 is in each case deflected in proportion to these gradients. These deviations, which corrupt the reflective mirror image 6, are registered by the camera 5. Since the light grid 4 is processed very accurately, the position and extent of the angle differences in the surface can be found exactly. Based on these angle differences which have been found, both the planarity and the ripple of the surface 2 can be calculated for a planar (nominal) sample.

In principle, the same rules apply to a curved surface (or a sphere etc.). However, the evaluation becomes more complex since the entire profile of the surface should be covered, so that it is not sufficient to carry out a local analysis of the deviation of the inclination in comparison with an ideal surface. In fact, based on at least two fixed points at which, for example, the curved rolled glass pane is supported, the inclination must be determined virtually strip by strip, so that an element of a polygon is obtained from the inclination multiplied by the width of the strip. The next element with its specific inclination is "fitted" to this element, and so on. This evaluation results in a large number of points on the profile which is to be measured. These points can then be represented as a curve, for a representation in the form of a graph. The three-dimensional coordinates can then be determined for the entire determined profile. The evaluation can be carried out by means of a line-scan camera in one direction, and by means of a matrix camera in two mutually perpendicular directions.

Since the angle differences are measured, the calculation of the profile for a planarity measurement advantageously excludes those (absolute) height differences (for example with respect to a null position of the apparatus) which would have been determined on the basis of the profile of the image as a result of an inclined arrangement of an otherwise planar surface using conventional methods, which work with sharp images. Inaccuracies in the positioning of the glass 2 thus, in principle, advantageously have no adverse affects on the measurement. Since the measurement, including the evaluation, is carried out in a very short time (0.1 to 2 seconds), and an analysis time interval for the surface 2 of a few milliseconds is sufficient for further processing, materials can be measured without any problems, and without any adverse affects, while they are being transported, for example on conveyor belts or the like, despite any vibration.

The light/dark values observed by the camera 5 are evaluated by an evaluation system (not illustrated) connected downstream from the camera. In this case, the evaluation of the intervals of the light grid 4 uses as a reference the light grid 4 which would have been reflected as the realistic mirror image in a completely planar surface. The evaluation system determines deviations from the light grid 4 in the mirror image 6, and uses this to calculate the respective local angle by which the measured surface 2 deviates from an ideal surface. Furthermore, it is possible to use incremental differences between adjacent strips as the basis for calculating the ripple on the surface, which often has a major influence on the optical properties of the glass, and is thus of major interest. Furthermore, if an appropriately designed device is provided on a rolled glass line, the ripple can be used to control the rolled glass plant. Since, at least to a first approximation (which is all that is relevant here), the light travels parallel from the grid 4 to the pane 2, it is advantageously unnecessary to record a reference image and to use this as the basis for the evaluation, since it is instead possible to assume the known structure of the grid 4 (that is to say the equidistant intervals of the grid 4). The measurement error resulting from this remains low, and the measurement time is short.

Figure 2:
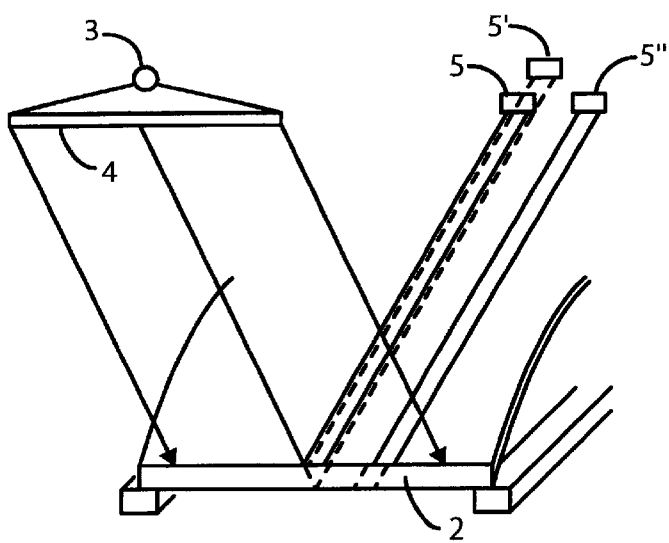
FIG. 2 shows a schematic front view of an apparatus according to the invention.
Figure 3:
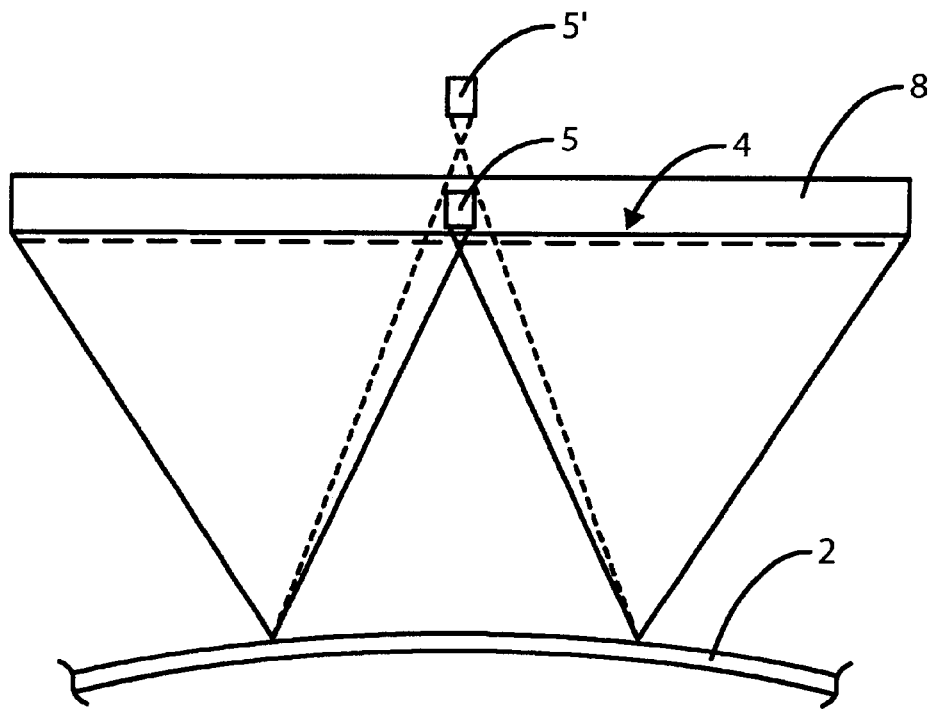
FIG. 3 shows a schematic side view of the apparatus shown in FIG. 2.

FIGS. 2 and 3 shows a front view and a side view of the components from FIG. 1 in a measurement apparatus. It can be seen that the camera 5 and the grid 4 are arranged essentially at the same height and include a relatively acute angle 8 of about 20°. The illustration in FIG. 2 shows the grid 4 parallel to, but slightly laterally offset with respect to, the glass plate 2, that is to say with a light beam (optical axis) that is incident at a slight angle to the normal to the surface 2, and the camera 5 in the extension of the emitted light that has been reflected on the surface 2 (optical axis). In FIG. 3, it can be seen that the section of the mirror image 6 which is observed by the camera 5 is dependent on the aperture of the camera 5. The section which is observed by the camera 5 is chosen such that it is 80 cm, so that 80 light/dark pairs are detected. If the number of observed strips increases or decreases, the evaluation apparatus deduces that the surface has a corresponding curvature like a lens (convex or concave). Deviations in the planarity can be measured rapidly and accurately even within this curved contour. It is possible to detect the surface topography of the test object 2 in a few milliseconds and without using any moving parts, with measurement accuracies of between 0.1 and 3 $\mu$m (ripple) and accuracies of less than 0.01 mm in the profile or the planarity over a measurement length of about 800 to 1600 mm being achievable in measurement times of 0.1 to 2 seconds.

In practice, the camera 5 is advantageously designed in a common assembly with the grid unit 4. The grid 4 is then arranged offset somewhat to the side and parallel with respect to an exactly opposite position, and the camera 5 is correspondingly offset in the opposite direction, preferably resulting in the two optical axes being at the same angle. This allows a particularly advantageous acute angle of a few degrees, for example 5°, to be achieved between the optical axes; however, the invention can also be used in practice with aperture angles of more than 5° and less than 90°. It is also possible to integrate the camera in the grid and, preferably, to arrange both on a normal to the surface 2.

It is self-evident that the described apparatus detects the profile in one direction, namely that which is located transversely with respect to the direction of the strips, that is to say in the longitudinal direction (bending) of the rolled glass 2. In the case of an essentially flat sample, for example a planar rolled-glass section onto which a decor has been printed, the inclination changes in comparison with an ideally planar profile can be used as a measure of the planarity. In a corresponding manner to that described above for the longitudinal profile and planarity, the transverse profile and planarity can also be determined by then subjecting the glass element 2 to the same measurement, but with relative rotation through 90° (either the system or the glass element is arranged rotated through 90°). Thus, for example, two arrangements 1 arranged one behind the other and rotated through 90° with respect to one another can be used to ensure that details about longitudinal and transverse planarity can be determined even in a continuous process, such as rolled-glass production, for example. Alternatively, it is also possible, using a cruciform grid (light/dark pairs in two, preferably mutually orthogonal, directions) to project an image onto the reflective surface of the glass element 2, this image being detected by a matrix camera. Then, the profile and deviations from the profile of an ideal sample in the longitudinal and transverse directions can subsequently be evaluated at the same time, by which means it is possible, in particular, to carry out measurements easily on surfaces 2 which are being conveyed continuously or intermittently.

It is thus possible to determine the profile of a three-dimensional sphere exactly and, likewise, to determine any gradient changes that occur in it, by differentiation. If the surface 2 is planar, the planarity can thus be determined very precisely; if the surface 2 is curved (or it represents a defined sphere), the bending quality and/or smoothness can thus be determined very precisely.

Figure 4:
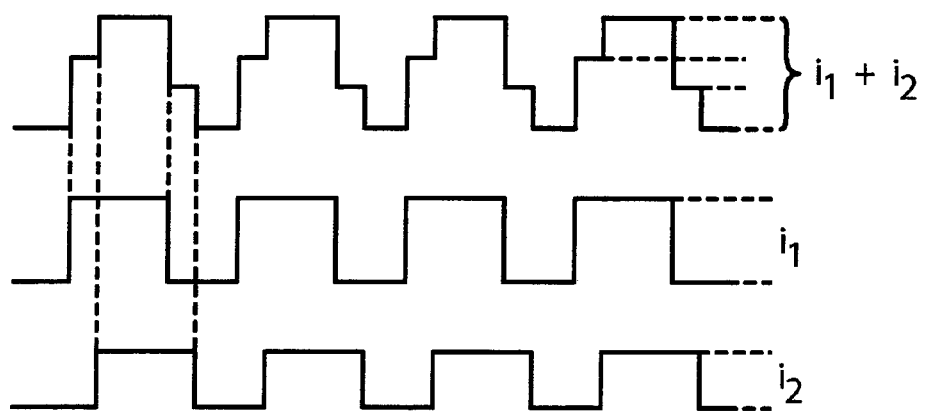
FIG. 4 shows a schematic illustration of a section of a signal which is detected by the camera and is then processed further.

As is shown by dashed lines in FIG. 2, one special feature of the glass plate 2 is that it produces two reflections, that is to say the grid 4 is reflected firstly on the upper face and secondly on the lower face of the glass plate 2. Since only the light beam which is not reflected on the upper face is reflected (partially) on the lower face of the glass plate, the intensity of the first reflection is somewhat stronger than the intensity of the second reflection. If the mirror image 6 produced in this way is observed from an angle, these two reflections are superimposed on one another. The angle for observation of the mirror image 6 is essentially governed by the compact size of the camera 5 and its aperture opening, and changes from pixel to pixel; this angular offset is taken into account in the evaluation (the path length change as a function of the angle is essentially cancelled out by the beam ratio of the image). It is possible by defocusing the camera 5 somewhat to detect the resultant of the superimposition of the two mirror images in the glass 2. The resultant of the light intensity i1 reflected from the upper face of the glass 2 and of the light intensity i2 reflected from the lower face of the glass is shown in FIG. 4. Since i1>i2, the resultant signal can easily be separated, so that the profiles of the upper face and lower face can be evaluated separately (as well as other, derived values such as the planarity, ripple, bending accuracy, height, thickness, etc.).

Alternatively, it is possible to arrange a second camera 5' behind the camera 5, with each of the two cameras being focused on one of the mirror images (that is to say on the grid), and with the detected data being evaluated appropriately. It is likewise possible to operate further line-scan cameras 5" parallel to the camera 5 and in this way advantageously to detect a large number of measured values in a narrow zone when operated in parallel, and subsequently process these measured values further. A line-scan camera can also be used to scan a surface area.

The arrangement of a second camera 5' at a different height than the camera 5, which is preferably observing the same image section, has yet another advantage. As already described above, a change in the number of strips observed can be caused by the surface having a lens shape. However, the same phenomenon occurs if—for whatever reasons—the height of the observed surface 2 is changed, and the observed image section correspondingly includes an increased or reduced number of strips. The different heights of the cameras 5, 5' makes it easy to correct height errors, and to take them into account appropriately in the evaluation of the profile.

Another alternative for the evaluation of materials that produce two reflections may be used, in particular, for tinted, for example green, glass. If green glass is illuminated (for example alternately) with red light and with green light from the grid, this light is absorbed to greatly different extents by the glass, so that the intensity of the light reflected from the lower face differs significantly. The different intensities for different light wavelengths make it simple to draw conclusions about the position of the reflection on the upper face or lower face of the glass. Alternatively, it is possible to use a color camera to observe the mirror image 6, as a result of which the sudden changes in the detected intensities for red, blue and green can easily be separated and can be associated with the appropriate face of the glass.

A further exemplary embodiment of an apparatus according to the invention will be explained in more detail with reference to FIGS. 5 to 7. In principle, the same reference characters denote the same parts as in the previous exemplary embodiments, which also means that parts which are substituted for one another can also be interchanged with one another.

The plan view in FIG. 5 shows that the apparatus has two elongated grids 4a, 4b, which are arranged directly side by side. The two grids 4a, 4b have two strips, which run obliquely (and not at right angles as in the case of the previous exemplary embodiment) to their longitudinal extent, in the present exemplary embodiment at an angle of 45°. The oblique angles of the two grids 4a, 4b are offset through 90° with respect to one another.

Two cameras 5a, 5b, which observe the same image section 7, are arranged at roughly the same height, approximately in the middle of the two mutually averted longitudinal sides of the grooves 4a, 4b. The observed object is an endless strip, for example of flat glass or of a partially reflective, partially transparent sheet of plastic. The cameras are inclined slightly in the direction of the image section 7. Each of the two cameras 5a, 5b in the present exemplary embodiment observes the reflection of the grid which is arranged further away from it. Alternatively, it would also be possible for the cameras to be arranged in the middle, between the grids.

The arrow A in FIG. 7 indicates a movement direction (flow) of the endless strip. X in FIG. 7 illustrates schematically a first fault type, which typically runs in the direction of the arrow A, that is to say when passing the image section 7, a region of the grids arranged somewhat further downstream (to the left in the figure) is initially recorded by the cameras 5a, 5b. The observed reflection then moves back again and continues in the other direction (in the opposite direction to the arrow A), before it can be seen to move back to the original region of the grid again. It would not be possible to detect this type of movement with the grid as in FIGS. 2 and 3 since the cameras would always have observed the same image. However, in the present apparatus, the camera 5a (on the left) initially detects a shift in the (uncompressed/unexpanded) grid image toward one side (for example to the right seen in the direction of the arrow A), then in the opposite direction, beyond the normal state, to a further inversion mark, before turning back to the original image once again. The direction of the movement observed by the camera 5b (on the right in FIG. 5) is exactly the reverse of this. Two line-scan cameras and two grids can thus be used to define a fault in the plane transversely with respect to the extent direction, as well. The two grids 4a, 4b are for this purpose provided with strips which are arranged obliquely both with respect to the feed direction A of the sheet and with respect to the mirror axis, between the line extent of the camera and the longitudinal extent of the grid.

A fault of the type indicated by Y in FIG. 7 is reliably detected by both cameras, by the compression and expansion of the observed image, determined as described using a phase-evaluating method.

It is self-evident that, accordingly, surface profiles and planarity profiles in which faults of types X and Y are superimposed, as is the case in reality, can also be determined reliably and cost-effectively using two line-scan cameras.

What is claimed is:

1. A method for measuring the profile of an at least partially transparent object including a first reflective surface and a second reflective surface, comprising the steps of:
   (a) projecting a defined pattern composed of at least two different light intensities repeatedly arranged adjacent to each other onto the object to be measured wherein the pattern produces a first mirror image of the pattern in said first reflective surface and a second mirror image of the pattern in said second reflective surface;
   (b) observing at least one area of the object by means of at least one camera wherein the observed area comprises a portion of said first mirror image of the pattern and a portion of said second mirror image of the pattern; and
   (c) evaluating output data of the observed area for determining changes in the profile of said object in the direction of said pattern.

2. The method as claimed in claim 1, wherein said at least one camera is set such that it records a resulting image composed of said first mirror image and said second mirror image of the pattern.

3. The method as claimed in claim 1 wherein said at least one camera observes a mirror image of said pattern via a mirror.

4. The method as claimed in claim 1 wherein said at least one camera is selected from the group consisting of line-scan cameras and matrix cameras.

5. The method as claimed in claim 1 wherein the pattern is composed of parallel, alternately light and dark strips.

6. The method as claimed in claim 1 wherein the pattern arranges squares of a first brightness and of a second brightness.

7. The method as claimed in claim 1 wherein the pattern is produced intermittently in time.

8. The method as claimed in claim 1 wherein said camera and a device for producing said pattern are accommodated in one physical unit.

9. The method as claimed in claim 1 wherein a three-dimensional representation resulting from a single observing step is produced in the evaluating step.

10. The method as claimed in claim 1 wherein optical axes between the pattern and the mirror image on the one hand and between the mirror image and the camera on the other hand, include the normal to the surface.

11. The method as claimed in claim 1 distinguished by an arrangement wherein optical axes between the pattern and the mirror image on the one hand, and between the mirror image and the camera on the other hand, include an angle which is less than 90°.

12. The method as claimed in claim 1 wherein the evaluating step comprises an integration of angle profiles between a first and a second measurement point from which it is possible to determine a geometric position of each point between the two measurement points.

13. The method as claimed in claim 1 wherein the evaluating step comprises calculating a discrepancy between a local inclination of the surface and a local inclination of an ideal surface.

14. The method according to claim 1 wherein the surfaces of the object to be measured are essentially planar and the evaluating step comprises calculating a local discrepancy from planarity.

15. The method as claimed in claim 1 wherein the evaluating step comprises calculating a deflection of the mirror image with respect to an ideal surface; and determining an inclination of the measured surface based on said calculated deflection.

16. The method as claimed in claim 15 wherein the evaluating step further comprises integrating the determined inclination values in order to determine a profile of the surface over the observed area.

17. The method as claimed in claim 15 wherein the evaluating step further comprises differentiating the determined inclination values in order to determine a ripple value of the surface over the observed area.

18. The method as claimed in claim 1 wherein at least one further camera observes the same area as said at least one camera and wherein said at least one camera is set to observe the mirror image in one of said first and second reflective surfaces and said further camera is set to observe the mirror image in the other of said first and second reflective surfaces.

19. A method for measuring the profile of a reflective surface of an object comprising the steps of:
   (a) projecting a first defined pattern composed of at least two different light intensities onto the surface to be measured, wherein said first pattern produces a first mirror image of said first pattern in the reflective surface;
   (b) projecting a second defined pattern composed of at least two different light intensities onto the surface to be measured wherein said second pattern produces a second mirror image of said second pattern in the reflective surface;
   (c) observing one area of the surface by means of a first line-scan camera;
   (d) observing said area by means of a second line-scan camera, said second line-scan camera being disposed in parallel to said first line-scan camera;
   (e) wherein said first and second patterns run obliquely with respect to each other and obliquely with respect to a line direction of either of said first line-scan camera and said second line-scan camera;
   (f) wherein said area comprises a first portion of said first mirror image of said first pattern and a second portion of said second mirror image of said second pattern; and (g) evaluating output data of said first line-scan camera and of said second line-scan camera of said observed area;

(h) wherein a lateral offset change between the data of said first line-scan camera and the data of said second line-scan camera is representative of an inclination change of the measured surface transversely with respect to said line direction of either of said first line-scan camera and said second line-scan camera.

20. An apparatus for determining the profile of a reflective surface of an object, comprising:

(a) first and second means arranged in parallel to each other for producing a first and a second light pattern, said first light pattern showing an angle with respect to said second light pattern;

(b) a first camera focused on a mirror image of said first light pattern;

(c) a second camera focused on a mirror image of said second light pattern;

(d) wherein said first camera and said second camera are aimed to the same area of said surface; and (e) a computer for processing output data of said first camera and said second camera;

(f) wherein the difference of the recorded data of said first camera and said second camera is used for calculating said profile of said surface with respect to two main axes of said surface.

* * * * *